United States Patent
Bokros et al.

Patent Number: 5,908,452
Date of Patent: Jun. 1, 1999

[54] PROSTHETIC HEART VALVE WITH IMPROVED BLOOD FLOW

[75] Inventors: Jack C. Bokros; John L. Ely; Michael R. Emken, all of Austin; Axel D. Haubold, Liberty Hill; T. Scott Peters, Georgetown; Jonathan C. Stupka, Austin; C. Thomas Waits, Pflugerville, all of Tex.

[73] Assignee: Medical Carbon Research Institute, LLC, Austin, Tex.

[21] Appl. No.: 09/027,358

[22] Filed: Feb. 20, 1998

Related U.S. Application Data

[63] Continuation of application No. 08/441,809, May 16, 1995, Pat. No. 5,772,694.

[51] Int. Cl.$^6$ .................................................. A61F 2/24
[52] U.S. Cl. ........................................... 623/2; 623/900
[58] Field of Search ................................ 623/1, 2, 900; 137/527

[56] References Cited

U.S. PATENT DOCUMENTS

| | | | |
|---|---|---|---|
| 3,727,240 | 4/1973 | Child | 3/1 |
| 4,328,592 | 5/1982 | Klawitter | 3/1.5 |
| 4,363,142 | 12/1982 | Meyer | 3/1.5 |
| 4,535,483 | 8/1985 | Klawitter et al. | 623/2 |
| 4,679,546 | 7/1987 | van Waalwijk et al. | 128/1 |
| 4,775,378 | 10/1988 | Knoch et al. | 623/2 |
| 4,799,930 | 1/1989 | Knoch et al. | 623/2 |
| 4,846,830 | 7/1989 | Knoch et al. | 623/2 |
| 4,995,881 | 2/1991 | Knoch et al. | 623/2 |
| 5,078,739 | 1/1992 | Martin | 623/2 |
| 5,171,263 | 12/1992 | Boyer et al. | 623/2 |
| 5,178,632 | 1/1993 | Hanson | 623/2 |

OTHER PUBLICATIONS

M. Knoch, H. Reul and G. Rau, "Flow Characteristics of Six Mechanical Heart Valve Prostheses in Aortic Position: Design Related Model Studies", *Surgery for Heart Valve Disease* (ed. Endre Bodnar), ICR Publishers, London (1990) ISBN 1–872743–00–5, pp. 590–601.

*Primary Examiner*—Mickey Yu
*Assistant Examiner*—Francis K. Cuddihy
*Attorney, Agent, or Firm*—Fitch, Even, Tabin & Flannery

[57] ABSTRACT

A prosthetic heart valve is shown which incorporates a valve body design and leaflet pivot arrangements that minimize turbulence and shear stresses having a tendency to generate thrombosis. A valve body having an axially curved entrance that is smoothly joined to a generally cylindrical body of extended axial length provides excellent fluid flow characteristics when combined with leaflets that can assume orientations perfectly aligned with the downstream flow of blood. By constructing such a pyrocarbon valve body which receives a metal ring at an appropriate location, suture rings that permit the tissue annulus to directly contact the exterior surface of the cylindrical valve body are accommodated.

13 Claims, 9 Drawing Sheets

PROSTHETIC HEART VALVE WITH IMPROVED BLOOD FLOW

This is a continuation of U.S. application Ser. No. 08/441,809, filed May 16, 1995, now U.S. Pat. No. 5,772,694.

BACKGROUND OF THE INVENTION

The present invention relates to heart valve prostheses, and in particular to mechanical heart valves having occluders that pivot and translate in moving between open and closed orientations.

DESCRIPTION OF THE PRIOR ART

Various types of heart valve prostheses have been developed which operate hemodynamically as a result of the pumping action of the heart. In the last decade, the bileaflet heart valve has generally become the mechanical valve of choice; however, some single occluder valves are still being offered. More recently, attention has also begun to be given to trileaflet valves. The study of blood flow through such multiple leaflet valves has convinced many investigators that it is very important that emphasis should be given to achieving designs with minimum turbulence and minimum pressure drop. It was generally believed that the shorter the axial length of a valve body was, the less would be the resistance to blood flow through the critical region of the valve, because the valve body was of course the region of greatest constriction. Many patented valve designs also concentrated on the shape and the placement of the occluders to minimize pressure drop and turbulence.

A number of U.S. patents, such as Nos. 4,363,142, 4,328,592, 5,178,632 and 5,171,623 illustrate heart valves having relatively short valve bodies of generally circular cross-section, some of which have rounded or radially outwardly flared upstream and downstream ends. U.S. Pat. No. 5,078,739 shows a heart valve having a sloping entrance end wherein the leaflets are mounted external of the valve body via resilient hinges embedded in the downstream end surface of the valve body. U.S. Pat. No. 4,775,378 shows a heart valve having a single occluder with a shallow S-shaped curvature that is alleged to promote the formation of a stable closed vortex on the suction side of the occluder; it is employed in combination with a valve body having a circular cross-section passageway that is continuously and increasingly constricted, i.e. its diameter decreasing, in the downstream direction. U.S. Pat. No. 4,846,830 discloses a bileaflet valve having a similar valve body wherein a pair of curved leaflets are employed which are arranged to create a venturi tube nozzle in the direction of downstream flow which is alleged to avoid vortex formation. U.S. Pat. No. 4,995,881 shows a valve having a similarly sloping entrance in combination with a pair of leaflets that are curved in the downstream direction so as to define a nozzle-shaped passage centrally between the two leaflets when they are in their open position orientation.

The more that such mechanical prosthetic valves have been studied, the more that investigators have concluded that the ideal prosthetic valve simply does not yet exist. From a materials standpoint, pyrolytic carbon has been determined to be adequately nonthrombogenic; as a result, the problem of combatting thrombosis in mechanical valves is presently felt to lie in preventing excess turbulence, high shear stresses and local regions of stasis. Blood is a very delicate tissue, and even minor abuses caused by turbulence and high shear stress can cause either thrombosis or emboli generation at local regions of stagnation. Therefore, it is felt that future improvement in the characteristic of thromboresistance in mechanical valves will likely be attained through the achievement of smooth, nonturbulent flow and the absence of stasis. Accordingly, the search for mechanical valves having such desirable characteristics has continued.

SUMMARY OF THE INVENTION

It has now been found that sources of turbulence in mechanical heart valves that can damage blood and lead to clotting are found to exist both at the leading edges of leaflets that are inclined to the direction of blood flow and at the leading edge of the valve body orifice itself. When a liquid must pass around a corner, as when entering an orifice, separation occurs, and turbulence and elevated shear stresses are created in such zone of separation. It has now been found that, by selecting a valve body of relatively extended axial length, by mounting leaflets therein so that, in their open orientation, the leaflets are individually free to generally follow blood flow and orient themselves so as to be parallel to the direction of downstream blood flow at any instant (to minimize the turbulence associated with the leaflets), and by also contouring the orifice inlet to eliminate that usual zone of separation that would otherwise be present, both head or pressure loss and the tendency for thrombosis generation are concomitantly decreased.

More specifically, it has been found that the entrance at the upstream end of the valve body should be essentially a section of a torus having a radius of curvature which is at least about 28% of the radius of the central passageway through the valve body and not greater than about 80%, that the valve body should have an average axial length at least about equal to the central passageway radius, and that the flaring toroidal entrance section should encompass essentially 360° of the circumference of the opening and extend for an axial distance not greater than about one-third of the average axial length of the valve body. Preferably the surface is at least about 30% of a quadrant of a torus which at its downstream end is preferably tangent to the remainder of the interior surface which is preferably generally cylindrical. Because the flow through such a valve body has been found to be a function of the fourth power of its diameter, the diameter of the passageway through such a valve body is maximized by using the thinnest valve body wall that is structurally adequate, in addition having the average axial length of the valve body be equal to at least about the radius of the interior cross-section. It has been found that the interior diameter can be advantageously maximized by allowing the exterior surface of the valve body to interface directly with the tissue annulus from which the natural valve has been excised. Accordingly, suture rings are employed which permit both mitral valves and aortic valves to be so located that the raw tissue annulus interfaces directly with the pyrocarbon outer surface of the valve body. The mitral valve suture ring may be a fairly straightforward design; however, for a replacement aortic valve, a suture ring is designed to permit the valve to be located above the aortic annulus in a location so that its upstream flared entrance will be slipped into the aortic orifice region so that its outer wall surface interfaces directly with the tissue.

DETAILED DESCRIPTION OF THE PREFERRED EMBODIMENTS

Figure 1:
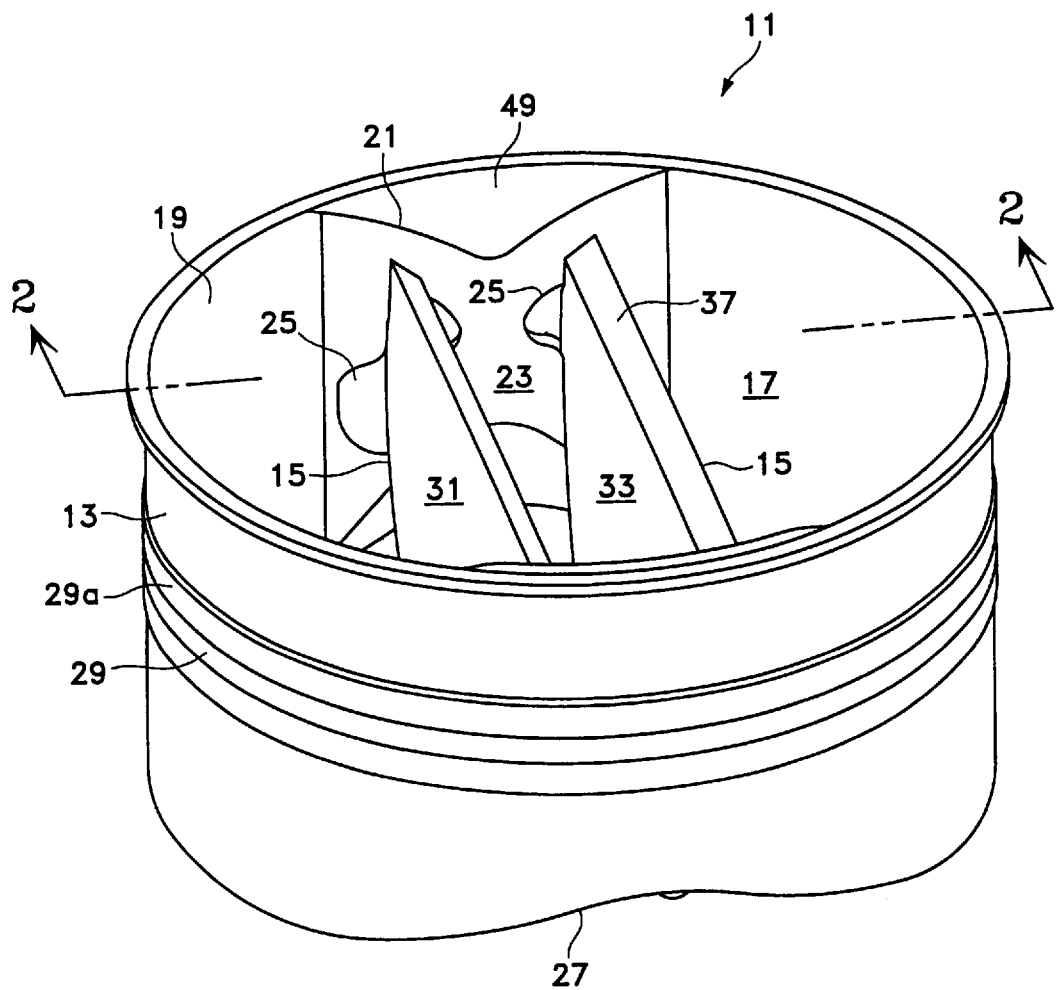
FIG. 1 is a perspective view of a bileaflet heart valve embodying various features of the present invention with the leaflets shown in the open position.

Illustrated in FIG. 1 is a preferred embodiment of a prosthetic heart valve 11 constructed so as to embody various features of the present invention. Very generally, heart valves having this construction have improved flow characteristics, particularly when the valve is in its fully open position, because the occluders can align parallel to the valve centerline or can align at slight deviations thereto depending upon instantaneous local variations in the blood flow path through the valve. As a result, such potential occluder or leaflet orientations minimize turbulence at the upstream edge surfaces thereof and substantially reduce drag and boundary layer separation along their major surfaces. This valve design also provides good washing characteristics which prevents stagnation and potential clotting. Importantly, heart valves of this design can incorporate pivot arrangements which exhibit a rapid response to change in the direction of blood flow, i.e. in initiating both opening and closing, and which reduce hemolysis or similar injury to blood cells because of the manner in which the occluders close against the valve body.

Figure 2:
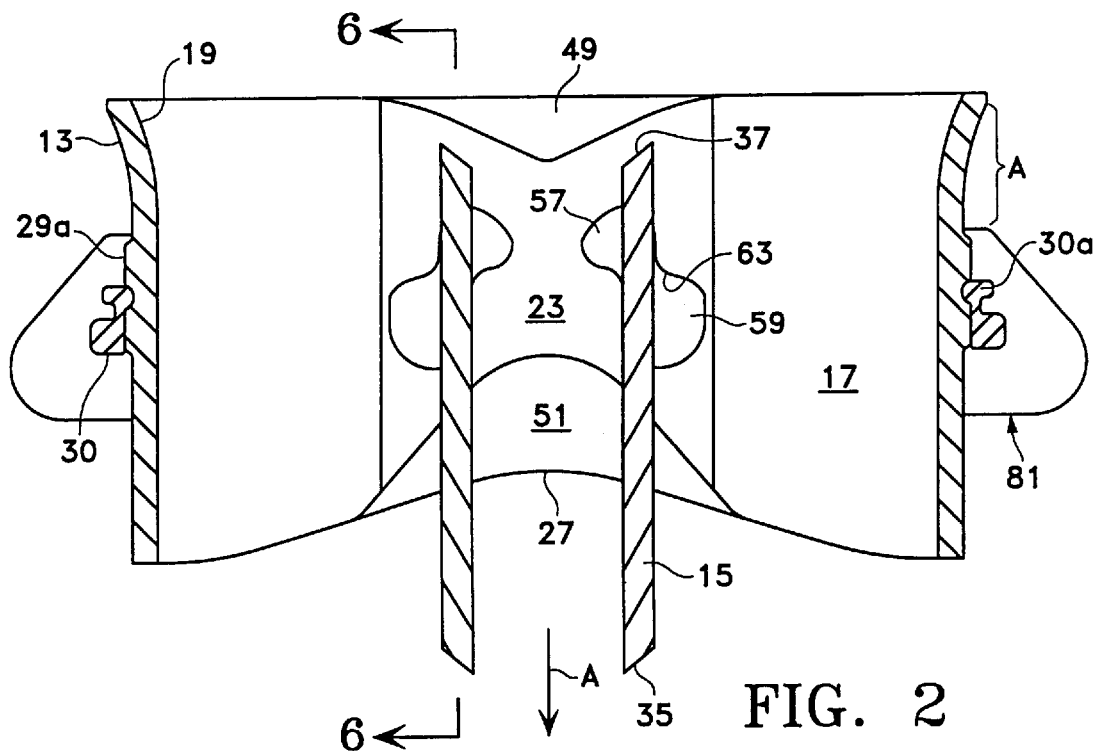
FIG. 2 is a sectional view taken generally along the line 2—2 of FIG. 1 showing the heart valve with the leaflets in the full open position, upon which a suture ring is installed that is designed to permit the valve to be mounted in the aortic position.
Figure 6:
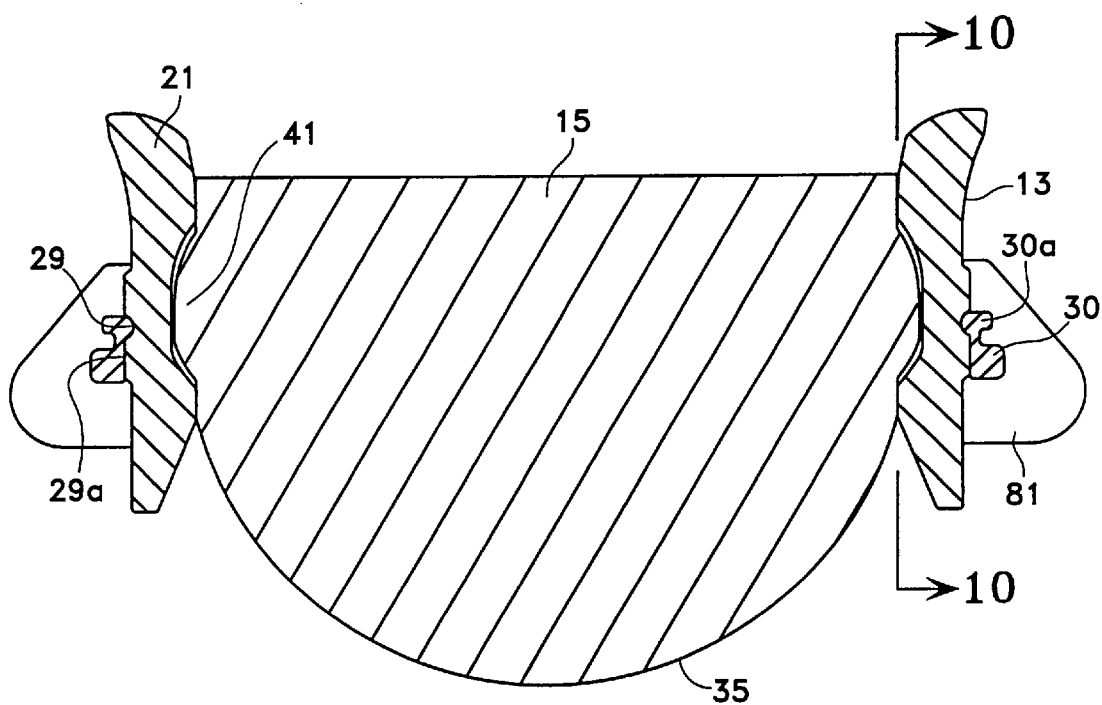
FIG. 6 is a vertical sectional view through the valve taken generally along the line 6—6 of FIG. 2 with the leaflet in the full open position.
Figure 5:
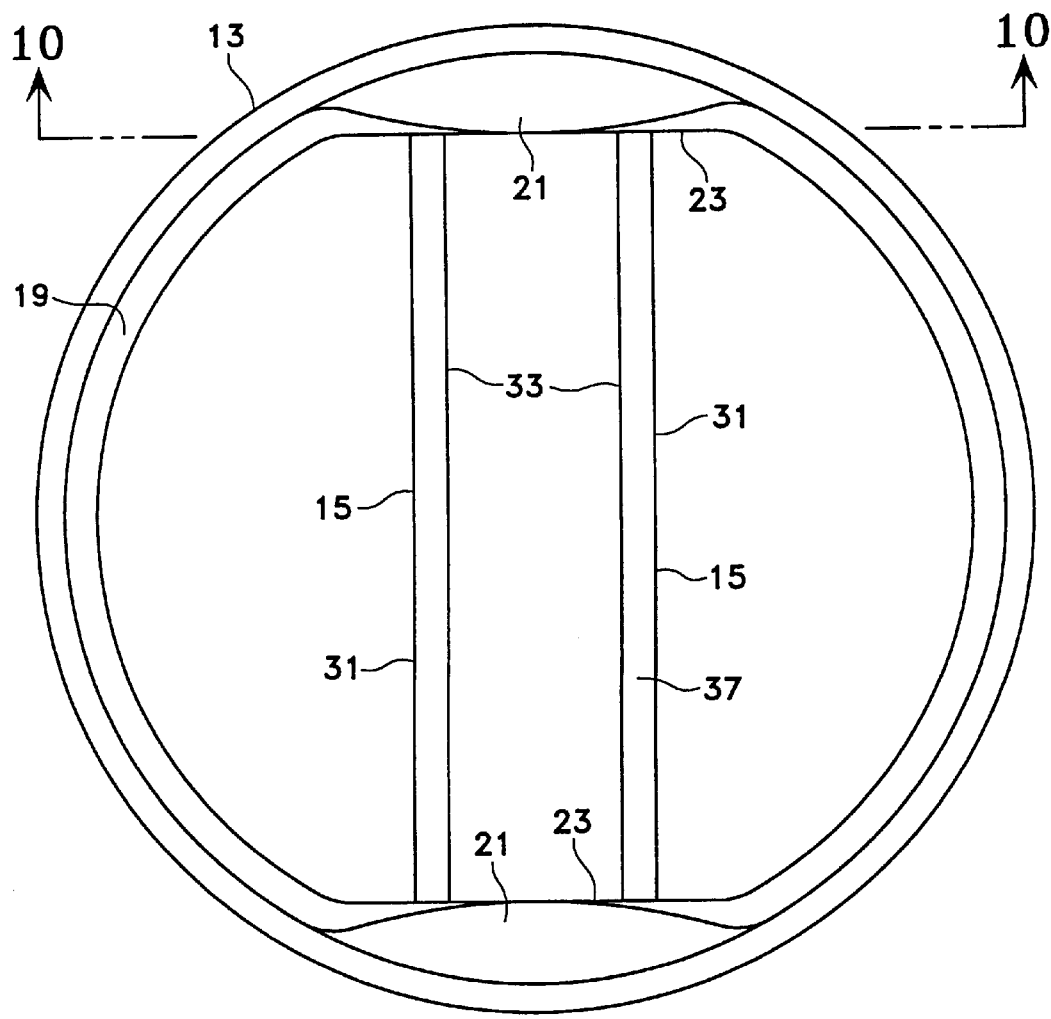
FIG. 5 is a plan view looking downward at the valve shown in FIGS. 1 and 2 with the leaflets in the full open position.

Heart valve 11 includes a generally annular valve body 13 that supports a pair of pivoting occluders or leaflets 15 which open to allow the flow of blood in the downstream direction, as indicated by the arrow A in FIG. 2, and to alternately close to prevent any substantial backflow of blood through the valve in the upstream direction. The valve body 13 defines a blood flow passageway in the form of its tabulated cylindrical interior wall surface 17 which lies downstream of a curved entrance region 19 at its upstream end, which is one of the important keys to the overall valve design that has now been found to result in substantially increased flow through the valve with low turbulence and substantially no generation of thrombosis. The details of the curved entrance region 19 which extends axially for a distance not greater than about one-third of the average axial length of the valve body are discussed hereinafter along with the operation of the valve. A pair of diametrically opposed, thickened wall sections 21, as best seen in FIG. 5, protrude inward from an otherwise right circular-cylindrical surface, creating what is referred to as a tabulated cylindrical surface as a result of the thickened sections 21 terminating in facing, parallel flat wall surfaces 23 in which pairs of cavities or recesses 25 are formed that function as one-half of the pivot arrangement which controls the opening and closing movements of the leaflets 15. Thus, the interior surface downstream of the curved entrance region 19 is generally rectilinear.

The valve body 13 preferably has a scalloped downstream profile so that there are, in effect, a pair of opposite shallow notches 27 formed in the contour of the valve body 13 in the regions just downstream of the thickened wall sections 21. In a bileaflet valve of this type, these notches 27 provide side openings into the central passageway which are aligned with the central blood flow passageway in the region between the outflow surfaces of the leaflets. Upon reversal of blood flow, backflowing blood will initially tend to laterally enter the valve body passageway through these side openings and will result in an initial upstream surge of blood into this central passageway region, creating forces which impinge upon the outflow surfaces of the leaflets and, along with fluid drag forces acting on the leaflets 15, promote prompt pivoting of the eccentrically mounted leaflets toward their closed position orientations. This function is described in greater detail in U.S. Pat. No. 5,308,361, the disclosure of which is incorporated herein by reference.

The exterior surface of the relatively thin valve body 13 in the region downstream of the flared entrance section 19 is substantially that of a surface of a right circular cylinder except for a slightly thickened central portion wherein a shallow groove 29 is formed between a pair of raised bands 29a. A metal stiffening attachment ring 30 of unique design (FIG. 2) which is formed with a plurality of circumferentially spaced apart inwardly protruding fingers 30a is mated therewith to add stability and rigidity to the valve body. The valve body itself is preferably made of a suitable material, such as pyrocarbon or pyrocarbon-coated graphite, as is well known in this art, which has sufficient resiliency that it can be deformed so as to permit the insertion of the pair of leaflets 15 in their operative locations. The metal ring 30 is also used to support the sewing ring of appropriate design, as broadly known in this art. Detailed examples of sewing or suture rings which can be employed are described in U.S. Pat. Nos. 4,535,483 and 5,178,633, the disclosures of which are incorporated herein by reference.

The thickened exterior bands 29a are strategically located in the downstream cylindrical section of the valve body spaced from the flared entrance section 19. As explained hereinafter in detail, the shallow groove 29 is located to accommodate the inwardly protruding fingers 30a of the metal ring 30 in either orientation as explained hereinafter. The groove 29, which is of arcuate cross section and constitutes the narrowest diameter on the exterior surface is located so that it is completely downstream of the fulcrums which are formed in recesses 25. This arrangement permits the suture rings to be accommodated in a location where the remaining tissue annulus will be in contact with a portion of the right circular cylindrical exterior surface of the valve body.

The leaflets 15 are preferably identical in form and shape and have two rectilinear, preferably flat, surfaces, i.e. an inflow surface 31 and an outflow surface 33. The inflow surface is arbitrarily defined as the surface which faces upstream when the leaflets are in the closed position, whereas the outflow surface is the opposite downstream facing surface. Each leaflet is preferably of substantially constant thickness such that the surfaces 31 and 33 are parallel to each other. Other leaflet configurations, such as sections of hollow cylinders of circular or elliptical cross-section may alternatively be employed, as discussed in more detail in U.S. Pat. No. 5,246,453, the disclosure of which is incorporated herein by reference.

Figure 4:
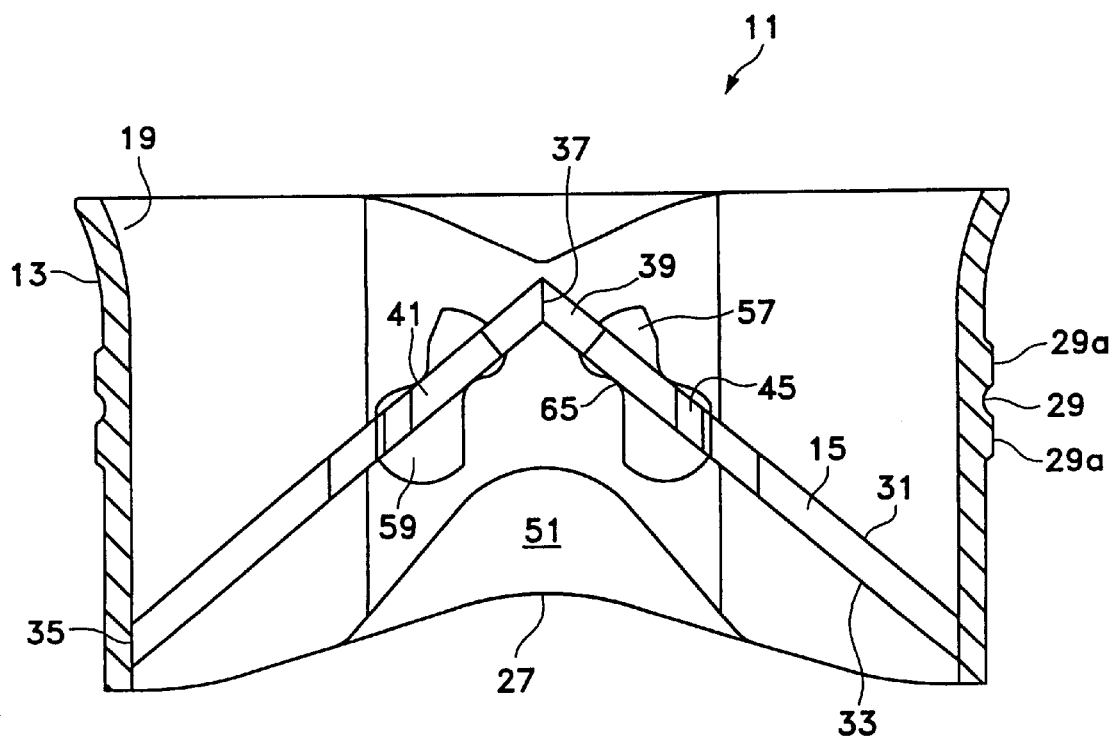
FIG. 4 is a view similar to FIG. 2, showing the leaflets in elevation and in their closed position, with the suture ring omitted.

Each leaflet 15 has a major arcuate downstream edge surface 35 which is shaped so as to abut and seat against the cylindrical side wall interior surface 17 of the valve body in the closed position. Each also has a mating minor edge surface 37 which is located at the upstream edge in the open position and which is preferably flat and formed at an angle so as to abut flush against the corresponding mating edge surface of the opposing leaflet in the closed position, as best seen in FIG. 4. The centerline plane is defined as a plane which includes the axial centerline of the passageway which is perpendicular to the flat wall surfaces 23. The pivot mechanism, as explained hereinafter, is constructed such that the leaflets 15 can assume an orientation precisely parallel to the centerline plane when blood is flowing downstream through the valve body passageway.

Figure 9:
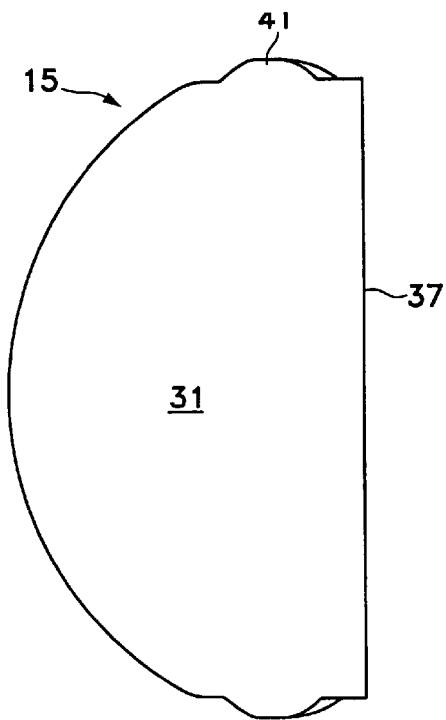
FIG. 9 is a front view of the leaflet of FIG. 8.
Figure 7:
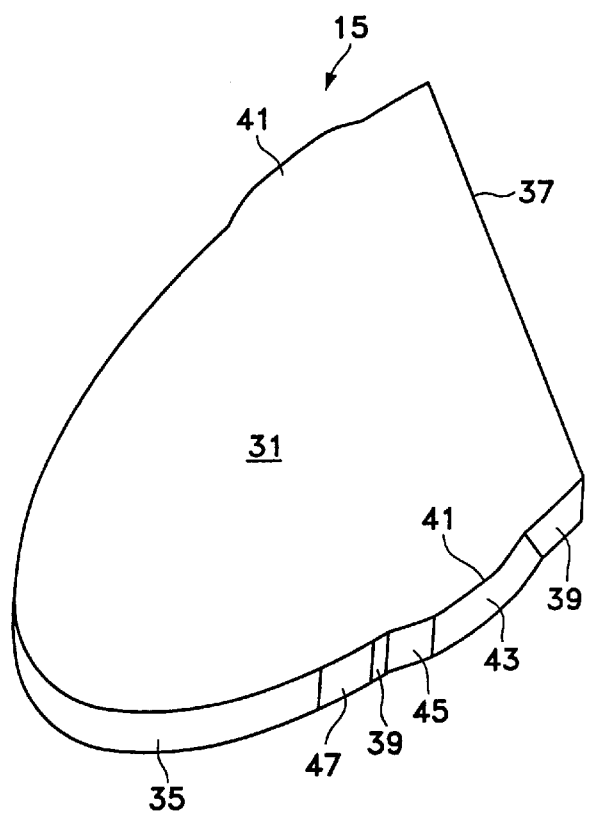
FIG. 7 is a perspective view of a leaflet from the valve of FIG. 1.
Figure 8:
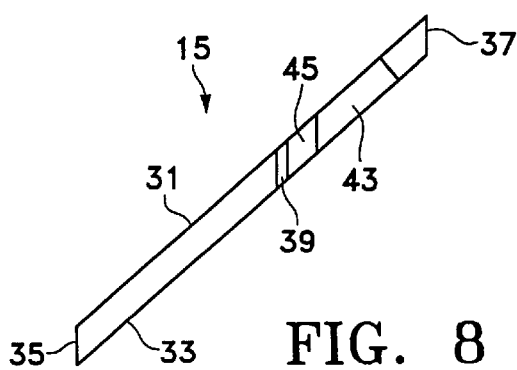
FIG. 8 is a side elevation view, reduced in size, of the leaflet of FIG. 7.

The leaflets 15, as best seen in FIGS. 7–9, each have a pair of intermediate straight edge surface regions 39 located between the minor mating edge surface and the major arcuate edge surface which are interrupted by a pair of laterally extending ears 41. The ears 41 have the same thickness as the flat leaflets and are elongated in an upstream-downstream direction viewed in their open orientation. The ears have upstream lateral edge surfaces 43 and downstream lateral edge surfaces 45 and are received in the cavities 25 in the flat wall regions of the thickened interior wall sections. The flat lateral edge surfaces 39 of the leaflets bear against the flat wall surfaces 23 surrounding the cavities and act as bearing surfaces during the movement of the leaflets between the open and closed position, and short transition surfaces 47 interconnect the surfaces 35 and 39.

As previously mentioned, the valve body 13 is formed with the thickened wall sections 21 in the regions where the cavities 25 are located, and preferably these thickened sections are formed with flaring transition surfaces, i.e. an upstream transition surface 49 and a downstream transition surface 51 which lead smoothly from the circular entrance region and the circular exit region of the valve body to the flat wall surfaces 23 wherein the cavities 25 are located. A surface such as the surface 49 may be referred to as a radial swept surface. As a result, the flow passageway through the valve body is generally circular in cross-section except for the two thickened sections 21 which extend inward to the flat wall surfaces 23. As previously indicated, the plane containing the centerline axis of the generally circular passageway that is oriented perpendicular to the flat surfaces 23 is referred to as the centerline plane and is frequently used for reference purposes throughout this specification.

Figure 10:
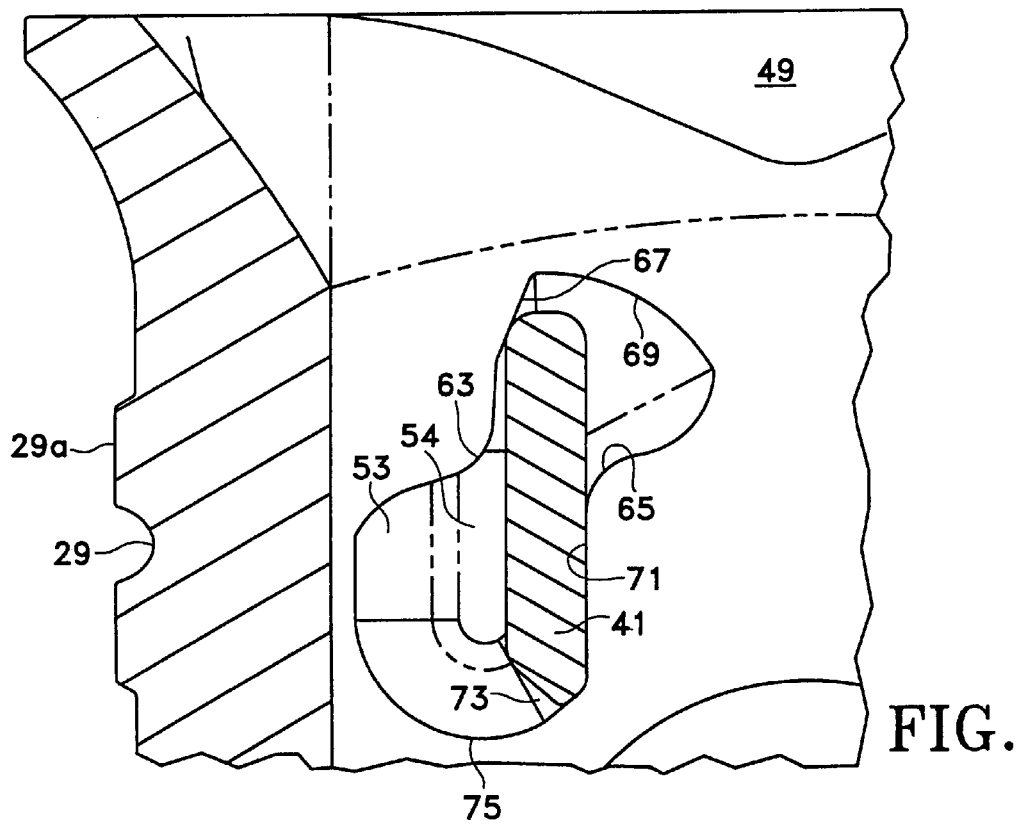
FIG. 10 is a fragmentary sectional view, enlarged in size, taken along the line 10—10 of FIGS. 5 and 6 with the sewing ring removed, which illustrates the freedom of the leaflet in question to rotate clockwise in the open position to assume an orientation of least resistance to downstream blood flow through the valve.
Figure 10A:
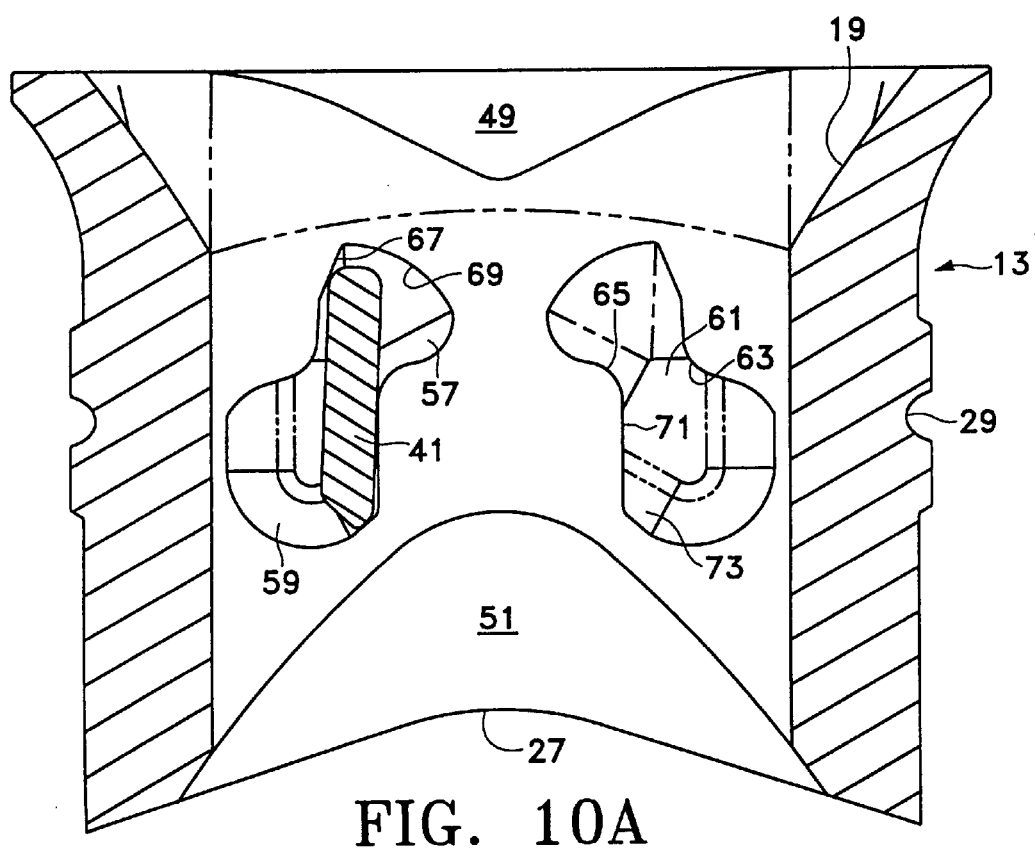
FIG. 10A is a full sectional view similar to FIG. 10 with the right-hand leaflet omitted and with the left-hand leaflet shown in the prerotation position.

For a bileaflet valve such as that illustrated, the cavities 25 formed in the valve body are in the form of pairs of side-by-side cavities which are mirror images of each other and which are respectively located on opposite sides of the centerline plane. As best seen in FIGS. 10 and 10A, the cavities each have a generally flat rear wall 54 which is surrounded by an irregular side wall contour 53 that assists in guiding the leaflets along the desired path in moving between the open and closed positions. Generally, the cavities are formed to have an upstream lobe 57 and a downstream lobe 59 on opposite sides of an intermediate throat section 61. The intermediate throat section is formed by a pair of curved fulcrums, termed an outward fulcrum 63 and an inward fulcrum 65 with respect to their location as reference to the centerline plane of the valve body. The upstream lobe 57 is formed with an inclined flat camming wall 67 which extends upstream from a location above the outward fulcrum 63 and joins a concavely curved wall section 69 which leads gradually downstream from the junction point. The downstream lobe 59 includes a flat wall section 71 immediately downstream of the inward fulcrum 65, which serves as a stop against which the leaflet ears 41 can assume a precisely parallel orientation in the full open position, and a downstream sloping section 73 which extends from the downstream end of the flat wall section to the arcuate bottom wall 75 of the downstream lobe.

The leaflets 15 are installed in the valve body 13 by squeezing the body at diametrically opposite locations so as to cause the flat wall sections 23 to spread sufficiently far apart to permit the leaflets to be fitted into the valve body so that the ears are received in the cavities. The method and apparatus disclosed in U.S. Pat. No. 5,336,259, issued Aug. 9, 1994, can advantageously be used for the insertion of the leaflets. When the squeezing force is removed, the valve body 13 returns to its original annular configuration leaving only the desired minimal clearance between the flat wall surfaces 23 of the valve body and the straight lateral edge surfaces 39 of the leaflets. The metal stabilizing ring 30 can be appropriately installed in the exterior circumferential groove 29 either following the installation of the leaflets or before installing the leaflets.

By designing the thickened bands 29a so that an inclined ramp is formed at the downstream edge of the downstream one of the two bands, it is possible to install the metal ring 30 by sliding it upward from the downstream end of the valve body 13 and allowing the fingers 30a to snap into place; however, it should be understood that the ring could be installed by shrink-fitting if desired.

Figure 2A:
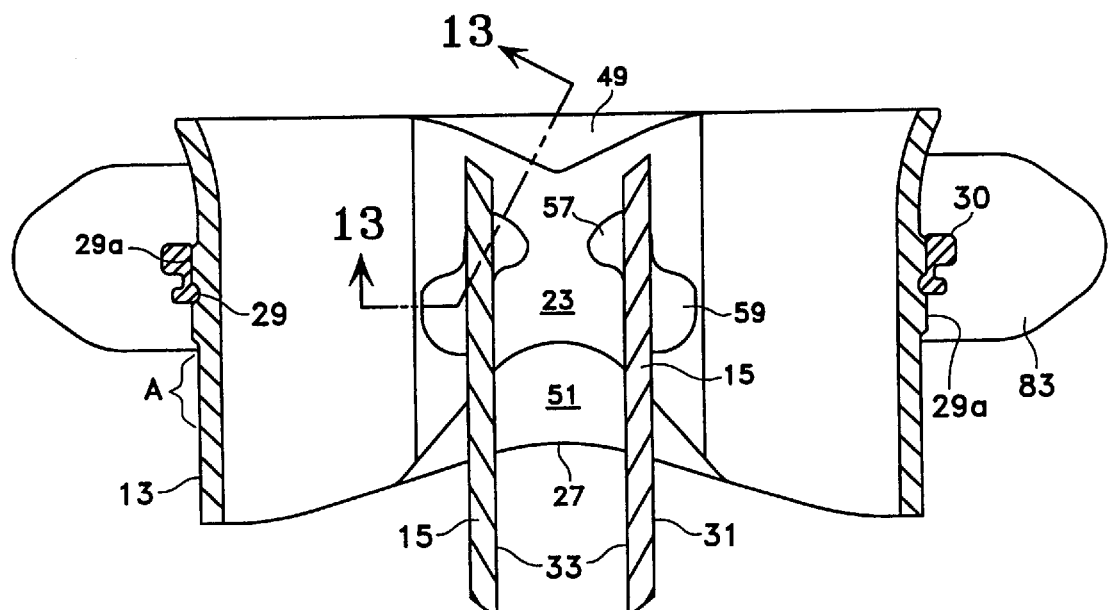
FIG. 2A is a sectional view taken generally along the line 2—2 of FIG. 1 showing the leaflets in the full open position, and with an alternative suture ring attached to the valve body.
Figure 3:
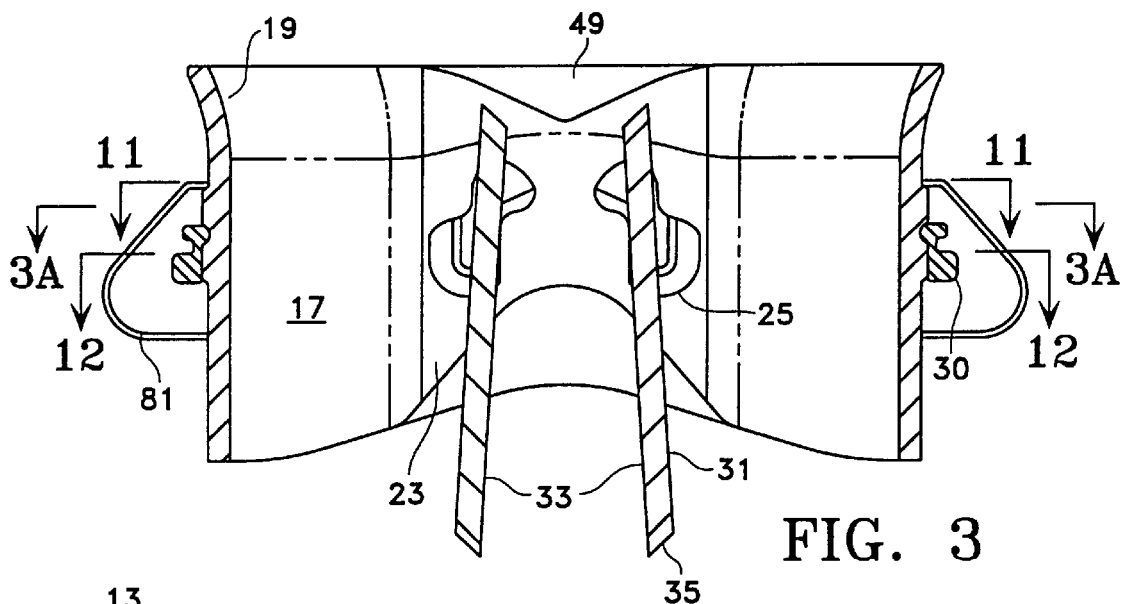
FIG. 3 is a view similar to FIG. 2 showing the leaflets in their prerotation orientation as they would be when the downstream flow of blood slows prior to reversal.
Figure 11:
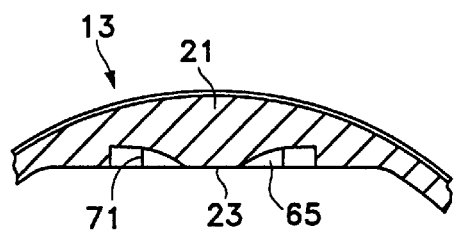
FIGS. 11 and 12 are fragmentary horizontal sectional views taken respectively along the lines 11—11 and 12—12 of FIG. 3, with the leaflets removed.
Figure 12:
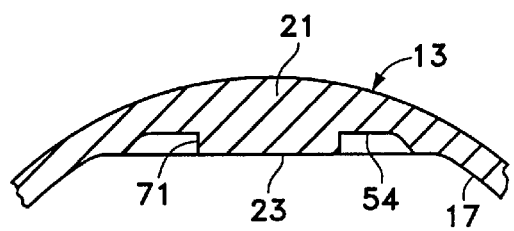
Figure 3A:
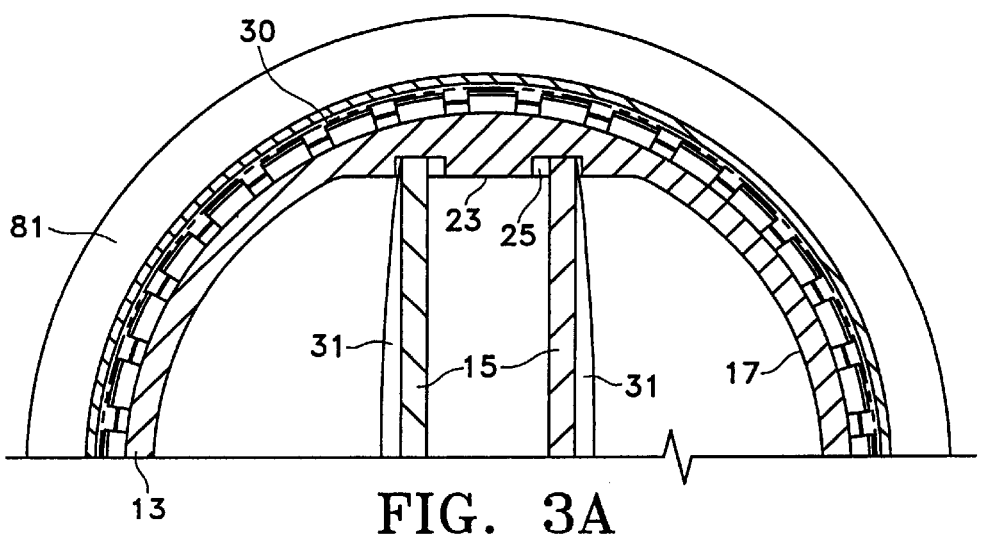
FIG. 3A is a fragmentary sectional view taken along the lines 3A—3A of FIG. 3.

The unique stiffening ring 30 is designed to facilitate the installation of either an aortic sewing ring or a mitral sewing ring exterior of the valve body 13, as best seen by comparing FIGS. 2 and 2A. In FIG. 2, an aortic sewing ring 81 is illustrated which is designed to leave the upstream exterior surface of the valve body free and clear to permit its insertion into the aortic annulus from which the defective natural valve was excised. For this installation, the stiffening ring 30 is slid onto the valve body 13 from the downstream end with the radially inward protruding fingers leading. As best seen in FIGS. 3 and 3A, these fingers 30a are connected by relatively thin necks to the main portion of the stiffening ring, and the fingers have curved radially interior faces which are proportioned to the curvature of the grooves 29.

Figure 15:
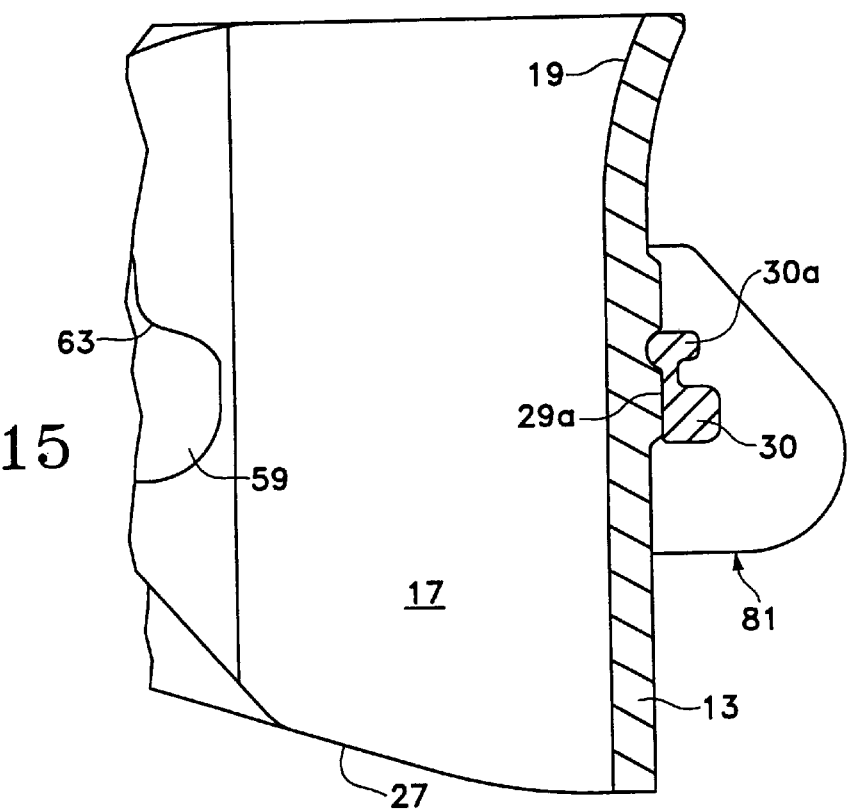
FIG. 15 is a view similar to FIG. 14 showing the aortic sewing ring attached.

When the leading projection section reaches the downstream band 29a flanking the groove 29, deflection of the fingers outward permits upstream travel to continue until the groove is reached, into which the projecting fingers then snap into place, as best seen in FIG. 15, with the main portion of the stiffening ring tightly surrounding the downstream cylindrical band 29a of the valve body and preferably placing it in at least slight compression.

Figure 13:
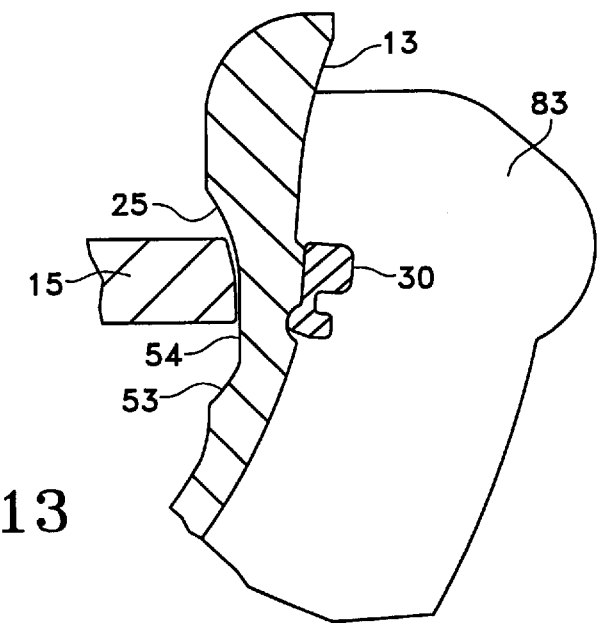
FIG. 13 is a fragmentary sectional view taken generally along the line 13—13 of FIG. 2A.

When the valve body is to be equipped with a mitral sewing ring 83 as depicted in FIG. 2A, such sewing ring is positioned so as to occupy a major portion of the exterior wall surface of the valve body 13 upstream of the groove 29, leaving the downstream section free for insertion into the tissue annulus from which the defective natural valve was excised. For this sewing ring, the stiffening ring 30 is installed with the opposite orientation, being slid upward from the downstream end of the valve body 13 leading with the ring section 30 having the cylindrical radially interior surface. When it reaches the downstream band 29a, it is forced upstream therepast, and the metallic projecting fingers 30a deflect and slide over the downstream band 29a as before. The ring section 30 bridges over the groove 29 onto the upstream band 29a, and sliding continues until the fingers 30a snap in place in the groove 29, at which time the ring is seated tightly about the upstream band 29a, as shown in FIGS. 2A and 13.

The depth of the shallow groove 29 is such that the thickness $T_2$ (FIG. 14) at the location of the groove is equal to at least about 85% of the thickness $T_1$ of the major cylindrical section of the valve body. The thickness $T_3$ at the location of the bands 29a need not be greater than about 120% of the thickness $T_1$. This strategic spacing and proportioning in a valve body 13 of the present design allows the wall thickness of the major portion of the valve body to be minimized, thus allowing a larger diameter opening for the passageway through the valve body. Generally, it is now felt that this interior diameter of the valve should be as large as tolerable (while still providing adequate structural strength) because the pressure loss through the valve increases relative to the fourth power of the diameter. Of course, each heart valve excised from the heart of a particular patient will vary with each patient, and therefore a surgeon should have available a set of prosthetic valves of different sizes generally ranging in exterior diameter from about 19 millimeters to 33 millimeters in diameter for fully grown adults. The reference measurement is that of the tissue annulus remaining after the defective natural valve has been excised.

The present valve design is such that it can be effectively installed so that the tissue annulus is in direct contact with the outer surface of the valve body 13 for valves that are installed both in the aortic position and in the mitral position. In this respect, it should be understood that, when installed, the tissue annulus of the patient will be in contact with the exterior surface of the valve body in the regions marked "A" in FIGS. 2 and 2A. One result of this arrangement is evident from FIG. 2A where it can be seen that the diameter of the substantially circular passageway through the valve is a very large percentage of the diameter of the tissue annulus, which is made possible because of the relative thinness of the major portion of the valve body wall, particularly in the region of the tissue annulus.

Alternatively, as indicated above the ring can be heated and shrink-fit onto the valve body so that the main body of the ring 30 is in contact with the desired band 29a. Such shrink-fitting allows greater compressive force to be applied to a pyrocarbon structure by such a metal ring and can improve the structural properties of the pyrocarbon which, as indicated above, is the preferred material of construction. Of course, if the ring is to be installed prior to the installation of the leaflets, a metal is chosen which has sufficient resiliency to return to its perfectly annular shape following removal of the squeezing force.

With the heart valve 11 operatively installed in a patient in either the mitral or the aortic position, when a pumping stroke of the heart causes downstream flow of blood through the valve, the two leaflets 15 will assume an open equilibrium position with respect to instantaneous path of the blood during conditions of high flow through the passageway. This may be an orientation where the leaflets 15 are aligned precisely parallel to the centerline plane, as illustrated in FIG. 2. However, should the dynamic forces within the valve body passageway vary, the leaflets may pivot to some extent to accommodate such variance; for example, the left-hand leaflet can rotate slightly clockwise to maintain a low energy position with respect to such an instantaneous change in the direction of the blood flow.

Figure 14:
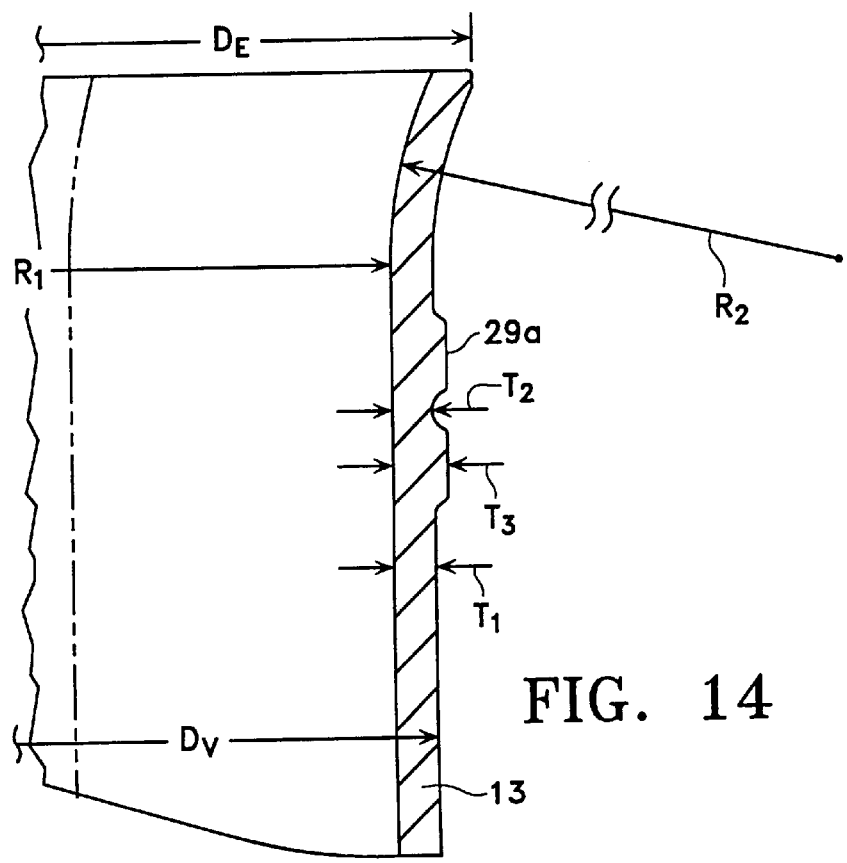
FIG. 14 is a fragmentary sectional view, enlarged in size, illustrating the valve body wall structure.

As previously indicated, the combination of this particular support of the leaflets 15, together with the shape and proportioning of the valve body 13 contributes to the achievement of smooth nonturbulent flow and the absence of stasis. The toroidal curvature of the curved entrance end 19 leading to a generally cylindrical valve body of substantial overall axial length has been found to achieve this desired end. More specifically, the construction of a valve body to have a curved entrance transition to a tabulated cylindrical, elongated passageway has been found to provide very low pressure drop for a passageway of a particular diameter. The average axial length of the valve is preferably at least 50% of the interior diameter thereof. The entrance section should constitute not more than about one-third of the average axial length of the valve body, and it should smoothly join with the downstream section, preferably being tangent thereto. The entrance section is preferably essentially a section of the surface of a torus. The torus is selected so that the interior diameter of the torus is between 80% and 120% of the diameter of the interior circular cross-section of the passageway through the valve body, and preferably between about 90% and 100%. Most preferably it is about 100% so that it will be substantially tangent to the right circular cylindrical downstream interior surface; if not, a short transition section is included. The radius of curvature of the circle that is revolved to create the torus is between about 28% and about 80% of the radius of the valve body and preferably between about 40% and about 65%. In FIG. 14, the interior radius of the valve body is marked "$R_1$", and the radius of curvature of the torus is marked "$R_2$". To facilitate aortic installation, the exterior diameter $D_E$ at the entrance end 19 should not be more than about 10% greater than the exterior diameter $D_V$ of the major cylindrical outer surface of the valve body; preferably, it is about 6–7% greater. By locating the stiffening attachment ring at a location in the valve body that is downstream of the pivot axes of the leaflets, i.e. downstream of the fulcrums where the contact for pivoting is defined, it can accommodate suture rings designed to have the tissue annulus directly lie in contact with the exterior surface of the valve body either upstream or downstream of such suture ring in the regions A in FIGS. 2 and 2A. Such an arrangement contributes to a thinner wall thickness and a larger interior diameter for the passageway.

Although at high rates of flow downstream through the valve, the leaflets can assume such precisely parallel alignment as described hereinbefore, when the peak downstream flow of blood has passed and it is slowing to approach zero flow, the drag of the bloodstream against the leaflets 15 can cause the ears 41 to move slightly downstream in the downstream lobes 59 which results in a pivoting of the leaflets a few degrees toward the closed orientation as shown in FIGS. 3 and 10A. Then, as the reverse flow of blood upstream through the valve begins, the leaflets immediately translate upstream, causing the ears to engage the camming surfaces 67 of the contoured wall of the upstream lobe 57 above the outward fulcrums 63 which causes the leaflets to very promptly pivot toward their closed positions. This upstream translational movement of the ear 41 in the cavity 25 assures that the pivoting of each leaflet toward its closed position orientation occurs very promptly upon the beginning of reverse flow and continues until the upstream edges of the leaflet ears reach the top of the upstream lobes 57. By this time, the leaflets 15 are oriented sufficiently transverse to the backflow of blood that the force of the blood against the outflow surfaces 33 becomes predominant, forcing the leaflets against the outward fulcrums 63 and continuing the pivoting motion. The final movement of the leaflets to the closed position is guided by the movement of the upstream lateral edge surfaces 43 of the ears along the downstream curved portion 69 of the upstream lobes 57 while the ears remain essentially in contact with the outward fulcrums 63.

In the fully closed position, as illustrated in FIG. 4, the mating edges 37 of the leaflets abut each other, and the downstream arcuate edge surfaces 35 abut the cylindrical interior surface 17 of the valve body. In this fully closed position, the force of the blood against the outflow surfaces 33 of the leaflets is borne by the seating of the arcuate edge surfaces 35 against the interior valve body wall 17 and by the ears 41 bearing against the outward fulcrums 63 which also directs forces so that the two mating edges 37 are pressed together in sealing arrangement. The proportioning of the leaflets 15 within the valve body 13 is such that some controlled leakage occurs in the cavities in an upstream direction past the ears. The dimensioning of the ears 41 and the cavities 25 is such that this pathway for controlled backflow tends to concentrate the leakage backflow in these regions where it achieves a cleansing action that positively guards against the occurrence of clotting at such locations. In this respect, the average clearance between the lateral edge surfaces of the ears and the rear walls 54 of the cavities is preferably at least about 50 microns to assure the desired cleansing action.

When the blood flow again reverses, as for example when the pumping stroke of the associated ventricle begins again, downstream displacement, i.e. translation, of the leaflets 15 initially occurs as a result of the force of the blood against the inflow surfaces 31. The ears 41 are quickly displaced so that they contact the inward fulcrums 65 and create an eccentric pivot axis about which opening pivoting motion quickly begins. Because of the shape of the downstream lobes, when blood flow reaches its maximum, the dynamic forces of the bloodstream in the passageway can cause the leaflets to assume a precisely parallel position where the ears 41 are juxtaposed flush against the flat walls 71 just downstream from the inward fulcrums 65.

The overall design of the valve is such that gross hemodynamics in terms of energy loss per cardiac cycle are superior to mechanical heart valves that are presently commercially available. Because blood is a very delicate tissue and even minor abuses caused by turbulence and high shear can result in thrombosis and emboli generation at local regions of stagnation, this valve design which avoids the creation of excessive turbulence and accompanying high shear stresses is particularly advantageous. Moreover, the design is such that the foregoing is accomplished while also maintaining prompt closing which achieves reduced regurgitation without increased turbulence.

Although the invention has been described with respect to certain preferred embodiments, which include what the inventors presently consider to be the best mode for carrying out the invention, it should be understood that various changes and modifications that would be obvious to one having the ordinary skill in this art may be made without departing from the scope of the invention which is defined by the claims appended hereto. For example, as earlier indicated, two curved rectilinear leaflets, three or more flat or curved leaflets, or even a single occluder could be used instead of the two flat leaflets that are shown in the drawings.

Particular features of the invention are emphasized in the claims which follow.

What is claimed is:

1. A prosthetic heart valve which comprises
    a generally tubular valve body having an upstream end, a downstream end and an interior sidewall which defines a central passageway therethrough for blood flow in a downstream direction, said passageway having an axial centerline and being generally circular in cross section,
    means associated with the exterior of said tubular valve body for mounting said valve in association with a human heart,
    at least one occluder having an inflow surface and an outflow surface, said occluder being mounted within said valve body to open and close so as to alternately permit flow of blood therethrough in a downstream direction when in an open orientation and to block reverse flow of blood in an upstream direction when in a closed orientation, and
    a pivot arrangement by which said occluder is associated with the interior of said valve body and by which said occluder is guided in movement between said open and closed orientations,
    said valve body having an upstream entrance end section formed with an interior surface that has a radius of curvature in a plane which contains said axial centerline between about 28% and about 80% of said central passageway radius, which entrance end section connects to a downstream cylindrical section,
    whereby downstream blood flow through said valve central passageway in said open orientation is of a streamlined nature.

2. The prosthetic heart valve of claim 1 wherein said downstream cylindrical section has a cylindrical exterior surface of exterior diameter $D_y$ extending to said downstream end, and wherein said upstream entrance end section has an exterior diameter that is at least about 6% greater than $D_y$.

3. The prosthetic heart valve according to claim 1 wherein said occluder has rectilinear outflow and inflow surfaces and wherein said pivot arrangement permits said occluder to assume an alignment so that said inflow and outflow surfaces are substantially parallel to said valve passageway axial centerline when said occluder is in said open orientation.

4. The prosthetic heart valve according to claim 3 wherein said at least one occluder comprises two leaflets, wherein said valve body is formed with a pair of diametrically opposed flat interior sidewall surfaces and wherein said downstream cylindrical section of said valve body terminates in a pair of diametrically opposed shallow notches which provide openings for the reverse flow of blood laterally into a central portion of the valve passageway, said lateral openings being aligned with said valve body flat interior sidewall surfaces.

5. The prosthetic heart valve according to claim 1 wherein said curved entrance end section is essentially a section of a torus having an interior diameter generally equal to between about 80% and 120% of a diameter of said generally circular central passageway.

6. The prosthetic heart valve according to claim 5 wherein said upstream entrance end section comprises a section of a torus extending axially for a distance between about 10% and about 33% of an average axial length of said tubular valve body.

7. The prosthetic heart valve according to claim 6 wherein said torus has an interior diameter equal to about a diameter of said generally circular central passageway and wherein said diameter of the upstream edge of said entrance end section is not more than about 10% greater than the exterior diameter of said downstream cylindrical section.

8. A prosthetic heart valve which comprises a generally tubular valve body having an interior sidewall which defines a central passageway therethrough for blood flow in a downstream direction, said passageway having an axial centerline and being generally circular in cross section, means associated with said tubular valve body for mounting said valve in association with a human heart, at least two leaflets, each having an inflow surface and an outflow surface, said leaflets being mounted in said valve body to open and close together to alternately permit flow of blood therethrough in a downstream direction when in an open orientation and to block the reverse flow of blood in an upstream direction when in a closed orientation, and a pivot arrangement by which said leaflets are guided in movement between said open and closed orientations, said pivot arrangement being such that said outflow and inflow surfaces may assume an alignment substantially parallel to said valve passageway axial centerline when said leaflets are in a fully open orientation, said valve body having an upstream entrance end section formed with an interior surface that has a radius of curvature in a plane which contains said axial centerline between about 28% and about 80% of said central passageway radius, which entrance end connects to a downstream cylindrical section, whereby downstream blood flow through said valve central passageway in said open orientation is of a streamlined nature and pressure drop across said heart valve is low.

9. The prosthetic heart valve according to claim 8 wherein said upstream entrance end section comprises a section of a torus having an interior diameter generally equal to between about 80% and 120% of a diameter of said generally circular central passageway.

10. The prosthetic heart valve according to claim 9 wherein said upstream entrance end section comprises a section of a torus extending axially for a distance between about 10% and about 33% of an average axial length of said tubular valve body.

11. The prosthetic heart valve according to claim 8 wherein the valve has exactly two leaflets, and wherein the downstream end of said valve body is formed with a pair of diametrically opposed shallow notches providing lateral openings for the reverse flow of blood into the central portion of the valve passageway, which lateral openings are generally aligned with axes upon which said leaflets pivot as established by said pivot arrangement.

12. A prosthetic heart valve for replacement of a defective aortic valve comprising a generally tubular valve body having an interior sidewall which defines a central passageway therethrough for blood flow in a downstream direction, said passageway having an axial centerline and being generally circular in cross section having a first radius, suture ring means located on the exterior surface of said tubular valve body for mounting said valve in association with a human heart, occluder means having an inflow surface portion and an outflow surface portion, which occluder means is mounted in said valve body to open and close to alternately permit flow of blood therethrough in a downstream direction when in an open orientation and to block the reverse flow of blood in an upstream direction when in a closed orientation, and a pivot arrangement by which said occluder means is guided in movement between said open and closed orientations, said valve body having an upstream entrance end section formed with an interior surface that has a radius of curvature in a plane which contains said axial centerline between about 28% and about 80% of said first radius, which entrance end section connects to a downstream cylindrical section, whereby downstream blood flow through said valve central passageway in said open orientation is of a streamlined nature so pressure drop across said heart valve is low, said entrance end section having an exterior circumferential surface that is concave and toroidal, and said suture ring means being so located axially along said exterior surface of said valve body that a tissue annulus raw edge lies in direct contact with said concave toroidal exterior circumferential surface when said heart valve is implanted in a patient.

13. The prosthetic heart valve according to claim 12 wherein a major portion of said upstream entrance end section of said valve body is of substantially constant thickness and wherein both said interior surface and said exterior surface of said entrance end section are in the form of at least 30% of a quadrant of a torus.

* * * * *